United States Patent [19]

Stern

[11] 4,347,257
[45] Aug. 31, 1982

[54] PROLACTIN SUPPRESSION IN MAMMALS

[75] Inventor: Warren C. Stern, Raleigh, N.C.

[73] Assignee: Burroughs Wellcome Co., Research Triangle Park, N.C.

[21] Appl. No.: 177,128

[22] Filed: Aug. 11, 1980

Related U.S. Application Data

[63] Continuation of Ser. No. 82,598, Oct. 9, 1979, abandoned.

[51] Int. Cl.³ .............................................. A61K 31/135
[52] U.S. Cl. ...................................... 424/330; 424/316
[58] Field of Search ............................... 424/330, 316; 260/570.5 C

[56] References Cited

U.S. PATENT DOCUMENTS 3,819,706 6/1974 Mehta ................................. 424/316
3,885,046 5/1975 Mehta ................................. 424/330

OTHER PUBLICATIONS

Stern, W. C., et al., Life Sciences, vol. 25, pp. 1717–1724, 1979.

Primary Examiner—Blondel Hazel
Attorney, Agent, or Firm—Donald Brown

[57] ABSTRACT

A method of suppressing prolactin secretion in humans by the administration of the compound of the formula

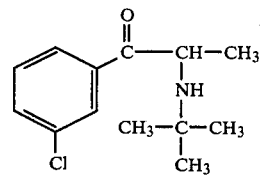

or a pharmaceutically acceptable salt thereof in a non-toxic, effective prolactin suppression amount (calculated as base) to a human in need thereof.

21 Claims, No Drawings

PROLACTIN SUPPRESSION IN MAMMALS

This is a continuation of application Ser. No. 82,598 filed Oct. 9, 1979, now abandoned.

BACKGROUND OF THE INVENTION

This invention is directed to a method of suppressing prolactin release (secretion) in humans by the administration to the humans of the compound of the formula I

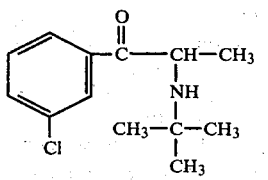

or a pharmaceutically acceptable acid addition salt thereof in a non-toxic, prolactin suppression amount (calculated as base) to a human in need thereof.

In U.S. Pat. Nos. 3,819,706 and 3,885,046, the compound of formula I (named m-chloro-α-t-butylaminopropiophenone) and salts thereof were disclosed as being antidepressants. It has now been found that the compound of formula I and its pharmaceutically acceptable salts thereof will effectively suppress the secretion of prolactin in humans.

A decrease in the secretion of prolactin is desired, such as in individuals with hyperprolactenemia, prolactin sensitive mammary cancer, amenorrhea resulting from hyperprolactenemia, galactorrhea, the post-partum period in which suppression of lactation is desired and any other circumstance in men or women in which a decrease in prolactin secretion would be beneficial.

Prolactin is a hormone that stimulates the secretion of milk and therefore the reduction of the levels of same in humans reduces the secretion of milk and would obviously find utility in cases where it is desired to prevent the production of milk in non-nursing mothers (e.g., women) at the time after the mother has given birth and the milk flow is at its greatest. However, it will also have utility in the treatment of humans who because of abnormalities produce prolactin and secrete milk, precursors thereof or other fluids from the mammary gland. This can occur in both females and males in certain instances.

Prolactin is also known to promote mammary gland development (see U.S. Pat. No. 4,150,147) and to promote functional activity of the corpus luteum (see Blakiston's Gould Medical Dictionary, Third Edition.)

The compound of formula (I) (the active ingredient) or a pharmaceutically acceptable salt thereof is preferably administered in unit dosage form to the human being treated.

The compound of formula (I) or salt in this invention may be administered orally, parenterally or rectally.

A pharmaceutical composition containing the compound of formula (I), or a pharmaceutically acceptable salt thereof, may be presented in discrete units such as tablets, capsules, ampoules or suppositories, each containing an effective prolactin or milk secretion suppression amount of the compound or salt.

For the treatment of humans to reduce (suppress) prolactin secretion, the preferred unit dosage of the compound of formula (I) or an acid addition salt thereof (estimated as the base) for oral administration, or administration as a suppository, is about 15 milligrams to 500 milligrams with the more preferred unit dosage being about 100 milligrams to 300 milligrams, and the most preferred unit dosage being about 125 milligrams to 250 milligrams. milligrams. All the above doses are given in terms of the weight of the compound of formula (I) in the form of its base, but as will be appreciated from the foregoing information, it may be administered in the form of a pharmaceutically acceptable acid salt thereof. Parenteral administration may be used and in this case the parenteral dose would be ½ the oral dosage.

The compound of formula (I) or pharmaceutically acceptable salts thereof may be presented as an oral unit preparation (for example as a cachet, tablet or capsule) containing one or more pharmaceutically acceptable carriers which may take the form of solid diluents such as lactose, cornstarch, micronized silica gel as well as other excipients known in the art.

It should be understood that in addition to the aforementioned ingredients, the pharmaceutical compositions of this invention may include one or more of additional ingredients such as diluents, buffers, flavouring agents, binders, surface active agents, thickeners, lubricants, preservatives, and the like. The formulations may be prepared by admixture of the ingredients, and, if necessary, shaping the resulting mass, and filling into suitable containers.

The compound used in this invention is preferably presented for use as a pharmaceutically acceptable salt. Examples of some of the pharmaceutically acceptable salts which can be utilized are salts of the following acids: hydrochloric, sulfuric, phosphoric and toluenesulphonic.

Reference should be had to U.S. Pat. Nos. 3,819,706 and 3,885,046, which are incorporated herein by reference hereto for a description of the preparation of the compound of formula (I), salts thereof, tablets, capsules, parenteral solutions and suppositories incorporating same.

I claim:

1. A method of suppressing elevated prolactin secretion in a human in which said suppression is medically desirable, which comprises administering to said human an effective non-toxic prolactin secretion suppression amount of a compound of the formula (I)

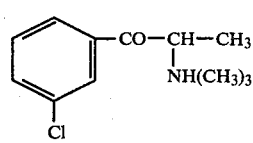

or a pharmaceutically acceptable acid addition salt thereof.

2. The method of claim 1 in which a pharmaceutically acceptable acid addition salt thereof is administered.

3. The method of claim 2 in which the salt is the hydrochloride salt.

4. The method of claim 1 in which the human is a woman.

5. The method of claim 2 in which the human is a woman.

6. The method of claim 3 in which the human is a woman.

7. The method of claim 4 in which the compound or salt is administered in a pharmaceutically acceptable carrier therefor.

8. The method of claim 5 in which the salt is administered in a pharmaceutically acceptable carrier therefor.

9. The method of claim 6 in which the hydrochloride salt is administered in a pharmaceutically acceptable carrier therefor.

10. The method of suppressing the secretion of milk, or other fluids from the mammary gland in a human in whom suppression is desirable, which comprises administering to said human a milk secretion suppression amount of the compound m-chloro-α-t-butylaminopropiophenone or a pharmaceutically acceptable acid addition salt thereof.

11. The method of claim 10 in which the human is a woman.

12. The method of claim 10 in which the salt is the hydrochloride salt.

13. The method of claim 10 in which the compound or salt is administered in a pharmaceutically acceptable carrier therefor.

14. The method of claim 11 in which the compound or salt is administered in a pharmaceutically acceptable carrier therefor.

15. The method of claim 12 in which the salt is administered in a pharmaceutically acceptable carrier therefor.

16. The method of claim 10 in which the salt is administered, the human is a woman and the salt is administered in a pharmaceutically acceptable carrier therefor.

17. The method of reducing prolactin levels in a human suffering from prolactin sensitive mammary cancer which comprises administering to said human so suffering an effective prolactin suppression amount of m-chloro-α-t-butylaminopropiophenone or a pharmaceutically acceptable salt thereof.

18. The method of claim 1 in which a tablet or capsule containing the compound or salt is administered.

19. The method of treating a human suffering from hyperprolactenemia which comprises administering to said human so suffering an effective prolactin suppression amount of m-chloro-α-t-butylaminopropiophenone or a pharmaceutically acceptable salt thereof.

20. The method of treating a human suffering from amenorrhea resulting from hyperprolactenemia, which comprises administering to said human so suffering an effective prolactin suppression amount of m-chloro-α-t-butylaminopropiophenone or a pharmaceutically acceptable salt thereof.

21. The method of treating a human suffering from galactorrhea which comprises administering to said human so suffering an effective prolactin suppression amount of m-chloro-α-t-butylaminopropiophenone or a pharmaceutically acceptable salt thereof.

* * * * *